United States Patent
Grompone et al.

(10) Patent No.: US 8,735,089 B2
(45) Date of Patent: May 27, 2014

(54) METHOD FOR SELECTING BACTERIA WITH ANTI-OXIDANT ACTION

(75) Inventors: Gianfranco Grompone, Paris (FR); Marie-Christine Degivry, Le Plessis Robinson (FR); Daniel Ramon Vidal, La Eliana (ES); Patricia Martorell Guerola, Picassent (ES); Nuria Gonzalez Martinez, Alaquás (ES); Salvador Genoves Martinez, Aldaia (ES); Sophie Legrain-Raspaud, Limours (FR); Isabelle Chambaud, Issy les Moulineaux (FR); Raphaelle Bourdet-Sicard, Palaiseau (FR)

(73) Assignees: Compagnie Gervais Danone, Paris (FR); Biopolis S.L., Paterna-Valencia (ES)

( * ) Notice: Subject to any disclaimer, the term of this patent is extended or adjusted under 35 U.S.C. 154(b) by 0 days.

(21) Appl. No.: 13/520,459

(22) PCT Filed: Jan. 8, 2010

(86) PCT No.: PCT/IB2010/000139
§ 371 (c)(1),
(2), (4) Date: Nov. 30, 2012

(87) PCT Pub. No.: WO2011/083353
PCT Pub. Date: Jul. 14, 2011

(65) Prior Publication Data
US 2013/0078187 A1    Mar. 28, 2013

(51) Int. Cl.
*C12Q 1/02* (2006.01)

(52) U.S. Cl.
USPC .......................................... 435/29

(58) Field of Classification Search
None
See application file for complete search history.

(56) References Cited

U.S. PATENT DOCUMENTS

2003/0190312 A1    10/2003    Kenyon et al.
2008/0229436 A1    9/2008    Reis et al.

FOREIGN PATENT DOCUMENTS

WO    03/002131    1/2003

OTHER PUBLICATIONS

Sem et al. (PLOS One, 7:e45417, 2012).*
Chen et al. (J. Cell Commun. Signal, 2:81-92, 2008).*
Uskova, Antioxidant Properties of Lactic Acid Bacteria-Probiotic and Yogurt Strains, Voprosy Pitania, 78, pp. 18-23, 2009.
Ikeda, Influence of Lactic Acid Bacteria on Longevity of *Caenorhabditis elegans* and Host Defense Against *Salmonella enterica* Serovar Enteritidis, Applied and Environmental Microbiology, 73, pp. 6404-6409, 2007.
Melov, Extension of Life-Span with Superoxide Dismutase/ Catalase Mimetics, Science, 289, pp. 1567-1569, 2000.
Bell, A Human Protein Interaction Network Shows Conservation of Aging Processes Between Human and Invertebrates Species, PLOS Genetics, 5, pp. E1000414, 2009.

* cited by examiner

*Primary Examiner* — Brian J Gangle
(74) *Attorney, Agent, or Firm* — Morgan, Lewis & Bockius LLP

(57) ABSTRACT

The present invention relates to a method using *Caenorhabditis elegans* for screening of food grade bacteria which have a protective effect against oxidative stress.

26 Claims, No Drawings

METHOD FOR SELECTING BACTERIA WITH ANTI-OXIDANT ACTION

RELATED APPLICATIONS

The present application is a U.S. National Phase Application of International Application No. PCT/IB2010/000139 (filed Jan. 8, 2010) which is hereby incorporated by reference in its entirety.

FIELD

The present invention is in the field of the methods for selecting food grade bacteria with anti-oxidative properties.

BACKGROUND ART

All living subjects maintain a reducing environment within their cells. However, due to the aerobic metabolism by the mitochondria and other factors, reactive oxygen-derived species such as peroxides and free oxygen radicals are produced. The reducing environment is preserved by enzymes such as superoxide dismutase, catalase and glutathion peroxidase. If the normal redox state is disturbed, the reactive oxygen species may damage all components of the cell, including protein, lipids and especially DNA. This imbalance between the production of reactive oxygen species and the ability to detoxify the reactive intermediates or repair the damage caused by the reactive oxygen species is called oxidative stress. In humans, oxidative stress is an important factor in aging and degenerative diseases associated with aging such as cancer, arthritis, diabetes, artherosclerosis, Lou Gehrig's disease, Parkinson's disease, heart failure, Alzheimers's disease, and Huntington's disease. The free-radical theory of aging states that organisms age because cells accumulate damage caused by reactive oxygen species over time.

In order to prevent the adverse effects of oxidative stress, there is a need for screening of dietary components which have anti-oxidative properties. Especially food grade bacteria, particularly lactic acid bacteria, are suitable anti-oxidative dietary components, since their use advantageously results in a long term effect of anti-oxidant action, via colonization of the intestinal tract.

The U.S. Pat. No. 6,884,415 discloses an antioxidant food product produced by fermenting a food product containing *Lactobacillus plantarum* having a superoxide dismutase (SOD)-like activity and a catalase (CAT) activity, in the presence of a manganese-containing natural material. Nevertheless, it is known that food grade bacteria, including lactic acid bacteria, can have anti-oxidative properties not dependent on the catalase or SOD activity.

The International Application WO 03/002131 discloses a *Lactobacillus fermentum* strain as anti-oxidative probiotic. The anti-oxidative properties of this strain were characterized in vitro by enzymatic tests and by measuring the glutathion red/ox potential.

The International Application WO 00/20013 discloses a *Lactobacillus* or *Propionibacterium* strain giving rise to increased amounts of propionic acid in the gut of a mammal for the manufacture of a medicament for reducing oxidative stress factors such as IL-6, reactive oxygen species and adhesion molecules.

*Caenorhabditis elegans* (*C. elegans*) is a free-living, transparent worm (nematode), which lives in temperate soil environments. *C. elegans* feeds on bacteria, particularly *Escherichia coli* OP50 strain. It has since been used extensively as a model organism for a variety of reasons. Strains are cheap and easy to breed and can be frozen. When subsequently thawed, they remain viable, allowing long-term storage. They have a short and reproducible life span. *C. elegans* has the advantage of being a multicellular eukaryotic organism that is simple enough to be studied in great detail. This worm has close to 40% of human orthologous genes among the whole genome, which make it an organism relevant for the human situation.

*Caenorhabditis elegans* has been used as animal model system for assessing the oxidative damage and effects on aging (Larsen, 1993, PNAS 90:8905-8909). The study has been carried out with a mutant strain having hyper-resistance to oxidative stress compared to its parental strain.

Further, Ikeda et al. (2007, AEM 73:6404-6409) have studied the effect of lactic acid bacteria on life span and *Salmonella* resistance of *C. elegans*. The authors suggest that *C. elegans* can be an appropriate model for screening probiotic bacteria strains (exerting beneficial effects on human health when ingested in sufficient numbers) or dietetic antiaging substances. However, resistance against oxidative stress was not assessed in this study. It is also known that the increased life span for *C. elegans* is related to the insulin pathway and related to orthologous genes in humans involved in the insulin-like growth factor and diabetes (Glenn et al., 2004, J Gerontol A Biol Sci Med Sci. 59:1251-1260).

SUMMARY OF THE INVENTION

The inventors have found that the animal model system *Caenorhabditis elegans* is a suitable model for screening the ability of food grade bacteria to counteract the damaging effects of oxidative stress. The screening assay can be performed in liquid media in microtiter plates to which bacteria are added, as well as on agar plates with lawns of bacteria as feed.

In particular, the effect of these food grade bacteria on prevention of damage occurring by oxidative stress, particularly in the form of oxidative reactive species, can be tested using *C. elegans*. A suitable way to impose oxidative stress to *C. elegans* was found to be the addition of hydrogen peroxide. The screening method of the present invention is relatively simple, yet the results obtained are relevant for the human situation. Finally, the method advantageously allows to select for strains of food grade bacteria with an overall anti-oxidative stress effect, without being restricted to the selection for a specific mechanism involved in an anti-oxidative effect such as the presence of a particular enzyme (e.g., CAT, SOD) or the release of a particular factor, as it is the case in the prior art.

DETAILED DESCRIPTION OF THE INVENTION

Screening Method using *Caenorhabditis elegans*

In one embodiment the present invention relates to a method for selecting food grade bacteria with anti-oxidative properties comprising:

a. a step of synchronizing the growth of *Caenorhabditis elegans* (*C. elegans*) worms;

b. a step of feeding said *C. elegans* worms on the food grade bacteria to be tested;

c. a step of incubating the *C. elegans* worms in the presence of oxidative stress;

d. a step of determining the viability of said *C. elegans* worms which were incubated in the presence of oxidative stress; and e. a step of selecting the food grade bacteria which provide the highest survival of said *C. elegans* in the presence of oxidative stress.

In another embodiment the present invention relates to the use of *Caenorhabditis elegans* in a method for selecting food grade bacteria with anti-oxidant properties.

The growth of *C. elegans* is synchronized because the method according to the present invention is advantageously carried out on worms being in the same growth state. Methods to grow and synchronize *C. elegans* worms are known in the art (In: W. B. Wood (ed) "The nematode *Caenorhabditis elegans*". Cold Spring Harbor Laboratory, Cold Spring Harbor, N.Y., pp 587-606; Chen et al., 2008, J. Cell Commun. Signal. 2:81-92). A suitable way to achieve synchronized growth is to harvest eggs from gravid adults and start with hatching the eggs. A suitable way to hatch the eggs is incubating them overnight in M9 medium (10% vol MRS (De Man, Rogosa and Sharpe medium), fluorodexouridine 100 μg/ml) plus 5 μg/ml cholesterol. Subsequently the $L_1$-stage worms can be isolated and grown as known in the art (In: W. B. Wood (ed) "The nematode *Caenorhabditis elegans*"; above cited). Preferably the worms are grown in the wells of a microtiter plate. Preferably the worms are grown without agitation during three days at 25° C. and at 80-85% relative humidity.

In a preferred embodiment of the method of the present invention, *C. elegans* mutant strain BA17 fem-1(hc17) (Nelson et al., 1978, Dev. Biol. 66:386-409) is used. This strain has advantageously inhibited fertility at 25° C., thereby making it easier to control its growth and reproduction.

In a preferred embodiment of step b. of the method of the present invention, *Escherichia coli* (*E. coli*), preferably *E. coli* OP50 (which is a normal food source for *C. elegans*) is used as a control feed.

Instead of control feed the worms can be grown in the presence of the food grade bacteria to be tested.

Preferably at least 50 worms are present per condition tested (presence or absence of oxidative stress), in order to find relevant differences between the different conditions.

When the worms have reached adult stage, preferably after 3 days culture, they can be incubated in the presence of oxidative stress. A suitable way to apply oxidative stress is by addition of hydrogen peroxide, preferably, at a concentration comprised between 1 mM to 20 mM final concentration, more preferably between 2 mM to 10 mM, even more preferably between 2 mM and 5 mM $H_2O_2$. 5 mM hydrogen peroxide is an optimal concentration. Preferably, as a control no $H_2O_2$ is added.

In a preferred embodiment of step c. of the method of the present invention, *C. elegans* are incubated in the presence of oxidative stress for 5 minutes to 48 h, more preferably 1 h to 10 h. 5 h is a suitable time for this incubation step.

One way of performing the incubation step in the presence of oxidative stress is in liquid media, for example in the wells of microtiter plates. This method has as advantage that many conditions can be tested simultaneously. Alternatively, the method can be performed on a solid medium, for example agar plates. This method is more laborious and time consuming that the microtiter assay but has as advantage that direct effects of the food grade bacteria on the oxidative stress conferring agent such as hydrogen peroxide, can be excluded.

In an embodiment of step c. of the method of the present invention, *C. elegans* worms can also be incubated in the absence of oxidative stress as a control. In a preferred embodiment of step d. of the method of the present invention, assessment of anti-oxidant resistance is read out as viability. This can be performed by microscopy. The worms are considered to be dead if they are paralyzed and no motion is observed.

In an embodiment of step d. of the method of the present invention, when there are *C. elegans* worms which are incubated in the absence of oxidative stress as a control at step c., then the viability of said *C. elegans* worms which are incubated in the presence of oxidative stress, is compared to the viability of said *C. elegans* worms which are incubated in the absence of oxidative stress.

The final step e. of the method of the present invention can be made by selecting the food grade bacteria which confer a high survival rate to the *C. elegans* worms in the presence of oxidative stress.

In a preferred embodiment of said step e., the survival of *C. elegans* in the absence of oxidative stress is assessed concomitantly and set to 100%.

In another embodiment of said step e., the effect of the food grade bacteria on the survival (or viability) of the *C. elegans* worms is compared with the effect of the control feed, such as *E. coli*.

Food Grade Bacteria

Food grade bacteria according to the present invention relate to bacteria selected from the group consisting of *bifidobacterium, lactobacillus, lactococcus, streptococcus, pediococcus, leuconostoc, oenococcus, enterococcus, aerococcus, carnobacterium, weisella, propionibacterium, bacillus, sporolactobacillus, corynebacterium* and *brevibacterium*.

Preferably, the food grade bacteria are lactic acid bacteria (LAB). Lactic acid bacteria according to the present invention relate to bacteria selected from the group consisting of *bifidobacterium, lactobacillus, lactococcus, streptococcus, pediococcus, leuconostoc, oenococcus, enterococcus, aerococcus, carnobacterium*, and *weisella*. More preferably the food grade bacteria are selected from the group consisting of *lactobacillus, streptococcus, lactococcus* and *bifidobacterium*.

The food grade strains tested can be grown as known in the art. By way of example, strains belonging to *Bifidobacterium, Lactobacillus* and *Streptococcus* genera are grown in MRS with cysteine, MRS and Elliker media, respectively.

In a preferred embodiment of the method of the present invention, for the microtiter plate assay, the food grade bacteria tested are viable.

In another preferred embodiment of the method of the present invention, the food grade bacteria are precultured and harvested in the logaritmic phase growth.

In another preferred embodiment of the method of the present invention, the cultures of the different food grade bacteria are added to the *C. elegans* comprising liquid growth medium at a final concentration of $1 \times 10^5$ cells/ml to $1 \times 10^8$ cells/ml, more preferable of $1 \times 10^6$ cells/ml to $1 \times 10^7$ cells/ml. $4 \times 10^7$ cfu/ml is a preferred concentration for an assay in liquid media. Alternatively, when *C. elegans* is tested on agar plates, the food grade bacteria to be tested can be present in the form of colonies or lawns on the agar plates.

In another preferred embodiment of the method of the present invention, the food grade bacteria are added to the *C. elegans* growth medium in the presence of an antibiotic which inhibits the further growth of the food grade bacteria. Further, an antibiotic has to be present to prevent further growth of the bacteria during the assay. Preferably, the worms are grown and incubated in the presence of an antibiotic, more preferably kanamycin, even more preferably kanamycin in a concentration of 10 to 100 μg/ml. Advantageously, kanamycin also inhibits the growth of the control feed *E. coli*. Other suitable antibiotics to inhibit some strains of lactobacilli are vancomycin, neomycine and erythromycin.

Application

The method of the present invention is preferably used to select strains of food grade bacteria which protect against oxidative stress and/or to prevent the damage imposed by oxidative stress. These food grade bacteria can subsequently be used in the manufacture of pharmaceutical compositions, nutritional supplements, and/or food compositions products.

Such compositions are suitable for humans suffering from oxidative stress. Especially the elderly are an appropriate target group, since the aged gut and the immunosenescence is prone to less effective resistance to the oxidative stress and production of ROS.

Example 1

Screening of Lactic Acid Bacteria on Survival of *C. elegans* with or without Oxidative Stress in Microtiter Plates 100 food grade strains belonging to *Bifidobacterium, Lactobacillus* and *Streptococcus* genera were tested for their anti-oxidative properties. These genera were grown in MRS with cysteine, MRS and Elliker media respectively. As the bioassay of the in vivo antioxidant activity was carried out with samples of living cells of different lactic acid bacteria, cells were recovered in the logaritmic phase growth. After the analysis of the growth curves, the optimal time for cell recovery was after 15 h of incubation at $DO^{600}=1$, 1.5 and 1.7 for *Streptococcus, Lactobacillus* and *Bifidobacterium* respectively. The cultures of the different lactic acid bacteria obtained as described above were added to the mixture at a final concentration of $4\times10^6$ cells/ml.

Subsequently, the sensibility of the 100 bacterial strains to kanamycin, an antibiotic used to avoid *Escherichia coli* growth, was analyzed. This antibiotic has to be present to prevent further growth of the bacteria during the assay. A concentration of 30 µg/ml kanamycin was found to be sufficient to inhibit *E. coli* OP50; 20% of the bacterial strains belonging to the genera *Bifidobacterium* and *Lactobacillus* were not inhibited by this antibiotic. However, since the bifidobacteria were not able to proliferate under the aerobic conditions, the presence of an antibiotic is not essential. Other suitable antibiotics to inhibit some strains of lactobacilli were vancomycin (250 µg/ml), neomycine (10-35 µg/ml), and erythromycine (1-100 µg/ml).

Experiments have been carried out with the *C. elegans* mutant strain BA17 fem-1(hc17) which has an inhibited fertility at 25° C. BA17 worms were synchronized by isolating eggs from gravid adults at 20° C., hatching the eggs overnight in M9 medium (10 vol % MRS, fluorodexouridine 110 µg/ml) plus 5 µg/ml cholesterol and isolating $L_1$-stage worms in the wells of a microtiter plate. The worms were grown without agitation during 3 days at 25° C. and 80-85% relative humidity. These larvae were transferred to a plate comprising M9 medium plus cholesterol and incubated for 3 days at 25° C. 80-85% humidity while undergoing control or experimental feeding. At least 50 worm were present per well.

After 3 days, when the worms had reached adult stage, oxidative stress was applied by addition of hydrogen peroxide $H_2O_2$ (2 mM, 3 mM and 5 mM) or without $H_2O_2$ (no stress control). Two controls have been used during this experiment: wells with *Escherichia coli* instead of a lactic acid bacterium as the control of bacterial feeding and wells with *E. coli* and 2 mM, 3 mM or 5 mM $H_2O_2$ as the control for oxidative stress. $H_2O_2$ at a concentration of 5 mM was found to be optimal. Anti-oxidant resistance was read out as viability, assessed after 5 h by microscopy. Worms were incubated in these conditions during 5 hours. To score for antioxidant capacity the worms were consider to be dead (stressed) if they were paralyzed.

In the absence of oxidative stress during the incubation time with *E. coli* the viability varied between 100 to about 90%. In an initial test the lactic acid bacteria had similar or better survival rates, which is indicative for a similar or improved longevity. Results for an effect of some selected strains are shown in Table 1 below.

TABLE 1

Effect of lactic acid bacteria feed on longevity of *C. elegans*.

| Strain | Viability % |
|---|---|
| S2A | 95.7 |
| S1B | 98.0 |
| S2B | 94.1 |
| S1C | 94.5 |
| S1D | 98.2 |
| S1E | 100.0 |
| S1F | 95. |
| S1G | 98.2 |
| S1H | 97.1 |
| L2A | 91.9 |
| L5A | 100 |
| L6A | 94.1 |
| L8A | 96.0 |
| L9A | 91.75 |
| *E. coli* OP50 | 89.5 |

The effect of 99 strains of lactic acid bacteria on survival of *C. elegans* under oxidative stress was tested with 2, 3 and 5 mM $H_2O_2$. It was found that 5 mM $H_2O_2$ was the best concentration to test for oxidative stress. In the presence of 5 mM $H_2O_2$, the viability of the worms in the presence of *E. coli* OP50 was about 93% compared to the absence of oxidative stress. This is indicative for a 93% protection against oxidative stress for *E. coli* OP50.

Table 2 below shows the effect of selected lactic acid bacteria on the level protection against oxidative stress, compared to the protective effect exerted by the control *E. coli* OP50 strain set at 100%.

TABLE 2

Level of protection against 5 mM $H_2O_2$ oxidative stress, conferred by some lactic acid bacteria compared to the protection conferred by *E. coli* OP50.

| Strain | Level of protection % |
|---|---|
| *E. coli* OP50 | 100 |
| Lactobacilli | |
| L8F | 14.6 |
| L9F | 21.6 |
| L10F | 9.7 |
| L1G | 102.5 |
| L3G | 7 |
| L4G | 30 |
| L6G | 23 |
| L7G | 95 |
| L8G | 18 |
| L9G | 81 |
| L10G | 77 |
| L1H | 70 |
| L4H | 87 |
| L5H | 6 |
| L7H | 3 |
| L8H | 9 |
| L10H | 8 |
| L8B | 76.8 |
| L9A | 18.7 |

TABLE 2-continued

Level of protection against 5 mM $H_2O_2$ oxidative stress, conferred by some lactic acid bacteria compared to the protection conferred by *E. coli* OP50.

| Strain | Level of protection % |
|---|---|
| L9B | 13.3 |
| L10B | 5.2 |
| L11B | 70.9 |
| L2C | 15.7 |
| L4C | 12.8 |
| L6C | 0.0 |
| L8C | 59.3 |
| L10C | 105 |
| L11C | 96.3 |
| L4D | 7.5 |
| L6B | 21.2 |
| L8B | 82.2 |
| L5C | 4.1 |
| L7C | 5.7 |
| L2D | 0.0 |
| L3D | 0.0 |
| L2E | 0.0 |
| L3F | 0.0 |
| L4F | 85.1 |
| L6F | 0.0 |
| L7F | 11.0 |
| L11A | 102 |
| L4B | 109 |
| L3B | 80.1 |
| L6A | 26.3 |
| L2A | 100 |
| L2B | 16.0 |
| L5A | 9.8 |
| L7B | 0.0 |
| L5B | 89.6 |
| L8A | 111 |
| L8D | 87.1 |
| L9D | 91.6 |
| L10D | 94.1 |
| L11D | 100 |
| L3E | 104 |
| L4E | 59.4 |
| L5E | 34.2 |
| L6E | 56.7 |
| L8E | 54.2 |
| L9E | 58.1 |
| L10E | 88.6 |
| L1F | 87.5 |
| L2F | 52.2 |
| L3A | 3 |
| L1B | 1 |
| *Bifidobacteria* | |
| B1B | 35.8 |
| B1C | 26.2 |
| B1D | 7.4 |
| B1E | 0.0 |
| B1G | 9.0 |
| B2G | 5.9 |
| *Streptococci* | |
| S2A | 84.3 |
| S1B | 61.5 |
| S2B | 85.0 |
| S1C | 45.8 |
| S1D | 93.8 |
| S1E | 89.7 |
| S1F | 8.2 |
| S1G | 11.7 |
| S1H | 42.3 |

It appears from the Table 2 above that, surprisingly, *Bifidobacterium* strains did not confer resistance to oxidative stress, while they confer a prolonged life span of *C. elegans* when cultured under anaerobic conditions (Ikeda et al., 2007; cited above). Further, surprisingly, only very few strains of *Streptococcus* and *Lactobacillus* were able to confer resistance to oxidative stress at a level higher than that of the control strain. The strains improving viability in the absence of oxidative stress were not necessarily the strains also giving the best protection against oxidative stress. This indicates that the improved effect of lactic acid bacteria on viability is not only caused by an effect on oxidative stress and that only very few, specifically selected strains of *Streptococcus* and *Lactobacillus*, have the ability to reduce anti-oxidative stress, compared to the control *E. coli* OP50.

Example 2

Effect of Selected Strains of Lactic Acid Bacteria on Resistance Against Oxidative Stress of Wild Type *C. Elegans* Grown On Agar Plates Wild type *C. elegans* N2 were grown on nematode growth medium (NG) agar plates for 5 days (to synchronize the worms) with lawns of *E. coli* OP50 or with lawns of selected strains of lactic acid bacteria from Example 1 conferring a protection against oxidative stress, and incubated with 3 mM $H_2O_2$ for 5 h. The viability of the worms was assessed just before and after the 5 h incubation and the percentage of survival under oxidative stress was determined by determining the percentage of worms that died during the incubation time. The results are shown in Table 3.

TABLE 3

Level of protection against 3 mM $H_2O_2$ oxidative stress, conferred by lactic acid bacteria relative to the protection conferred by *E. coli* OP50 on agar plates.

| Strain | Protection against oxidative stress, % relative to *E. coli* OP50 |
|---|---|
| L10C | 162 |
| L11D | 162 |
| L3E | 106 |
| L11C | 57 |
| L4B | 69 |
| L8A | 0 |
| S1D | 38 |
| S1E | 49 |

In the assay with agar plates (instead of wells) specific strains of lactic acid bacteria were shown to exert a protective effect against oxidative stress, but not all strains tested in Example 1 turned out to be effective against oxidative stress. Of the 99 strains 3 *lactobacillus* strains, 10C, 11D and 3E were effective against oxidative stress.

Of the *Streptococcus* strains tested (S2B, S1E and S1D) none were able to protect against oxidative stress at a level above *E. coli* OP50 in the agar plate assay.

It appears from the foregoing that the agar plate method turns out to be more selective than the microtiter plate assay. Since the agar plate assay is more laborious and time consuming than the microtiter plate assay, the agar plate assay can be suitably used when only few food grade strains are tested.

The invention claimed is:

1. A method for selecting food grade bacteria with anti-oxidative properties comprising:
   a a step of synchronizing the growth of *Caenorhabditis elegans* (*C. elegans*) in the presence of an antibiotic;
   b a step of feeding the *C. elegans* on the food grade bacteria to be tested in the presence of an antibiotic;
   c a step of incubating the *C. elegans* in the presence of oxidative stress and an antibiotic, and incubating a control group of *C. elegans* in the absence of oxidative stress as a control and in the presence of an antibiotic;

d a step of determining the viability of said *C. elegans* which were incubated in the presence of oxidative stress and comparing the viability of said *C. elegans* which were incubated in the presence of oxidative stress to the viability of said control *C. elegans* worms which were incubated in the absence of oxidative stress; and e a step of selecting the food grade bacteria which provide the highest survival of said *C. elegans* in the presence of oxidative stress.

2. The method according to claim 1, characterized in that said *C. elegans* are *C. elegans* mutant strain BA17 fem-1 (hc17).

3. The method according claim 1, characterized in that said *C. elegans* are grown in the wells of a microtiter plate.

4. The method according to claim 1, characterized in that the *C. elegans* are grown on agar plates.

5. The method according to claim 1, characterized in that the control group of *C. elegans* receives an *Escherichia coli* feeding.

6. The method according to claim 1, characterized in that said antibiotic is kanamycin.

7. The method according to claim 1, characterized in that said oxidative stress is applied by addition of hydrogen peroxide ($H_2O_2$).

8. The method according to claim 1, characterized in that said step c is performed for 5 minutes to 48 h.

9. The method according to claim 1, characterized in that said food grade bacteria are strains belonging to lactic acid bacteria.

10. The method according to claim 5, characterized in that said *Escherichia coli* is *E. coli* OP50.

11. The method according to claim 6, characterized in that said kanamycin is at a concentration of 10 to 100 μg/ml.

12. The method according to claim 7, characterized in that the concentration of $H_2O_2$ is 1 to 20 mM after it is added.

13. The method according to claim 8, characterized in that step c is performed for 1 h to 10 h.

14. A method for selecting food grade bacteria with antioxidative properties comprising:

a synchronizing the growth of *Caenorhabditis elegans* (*C. elegans*);

b feeding the *C. elegans* on the food grade bacteria to be tested;

c incubating the *C. elegans* in the presence of oxidative stress and incubating a control of *C. elegans* worms in the absence of oxidative stress as a control, wherein said oxidative stress is applied by addition of hydrogen peroxide ($H_2O_2$);

d determining the viability of said *C. elegans* which were incubated in the presence of oxidative stress and comparing the viability of said *C. elegans* which were incubated in the presence of oxidative stress to the viability of said *C. elegans* which were incubated in the absence of oxidative stress; and e selecting the food grade bacteria which provide the highest survival of said control *C. elegans* in the presence of oxidative stress.

15. The method according to claim 14, characterized in that said *C. elegans* are *C. elegans* mutant strain BA17 fem-1 (hc17).

16. The method according to claim 14, characterized in that said *C. elegans* are grown in the wells of a microtiter plate.

17. The method according to claim 14, characterized in that the *C. elegans* are grown on agar plates.

18. The method according to claim 14, characterized in that the control group of *C. elegans* receives an *Escherichia coli* feeding.

19. The method according to claim 18, characterized in that said *Escherichia coli* is *E. coli* OP50.

20. The method according to claim 14, characterized in that the *C. elegans* are grown and incubated in the presence of an antibiotic.

21. The method according to claim 20, characterized in that said antibiotic is kanamycin.

22. The method according to claim 21, characterized in that said kanamycin is at a concentration of 10 to 100 μg/ml.

23. The method according to claim 14, characterized in that the concentration of $H_2O_2$ is 1 to 20 mM after it is added.

24. The method according to claim 14, characterized in that said step c is performed for 5 minutes to 48 h.

25. The method according to claim 24, characterized in that step c is performed for 1 h to 10 h.

26. The method according to claim 1, characterized in that said food grade bacteria are strains belonging to lactic acid bacteria.

* * * * *